United States Patent [19]

Ellis, Jr. et al.

[11] Patent Number: 5,118,886
[45] Date of Patent: Jun. 2, 1992

[54] CYANO- AND POLYCYANOMETALLOPORPHYRINS AS CATALYSTS FOR ALKANE OXIDATION

[75] Inventors: Paul E. Ellis, Jr., Downingtown; James E. Lyons, Wallingford, both of Pa.

[73] Assignee: Sun Refining and Marketing Company, Philadelphia, Pa.

[21] Appl. No.: 758,148

[22] Filed: Sep. 12, 1991

[51] Int. Cl.$^5$ ...................... C07C 29/50; C07C 31/12
[52] U.S. Cl. .................................. 568/910; 568/910.5
[58] Field of Search .............................. 568/910, 910.5

[56] References Cited

U.S. PATENT DOCUMENTS

| | | | |
|---|---|---|---|
| 3,816,548 | 6/1974 | Williams et al. | 568/910 |
| 4,028,423 | 6/1977 | Brownstein et al. | 568/910 |
| 4,459,427 | 7/1984 | Middleton et al. | 568/910 |
| 4,895,680 | 1/1990 | Ellis et al. | 568/910 |
| 4,895,682 | 1/1990 | Ellis et al. | 568/910.5 |
| 4,900,871 | 2/1990 | Ellis et al. | 568/910.5 |
| 4,912,266 | 3/1990 | Sanderson et al. | 568/910 |
| 4,912,267 | 3/1990 | Sanderson et al. | 568/910 |
| 4,922,034 | 5/1990 | Sanderson et al. | 568/910 |
| 4,978,799 | 12/1990 | Sanderson et al. | 568/910 |

Primary Examiner—J. E. Evans
Attorney, Agent, or Firm—Q. Todd Dickinson; Donald R. Johnson

[57] ABSTRACT

Alkanes are oxidized by contact with oxygen-containing gas in the presence as catalyst of a metalloporphyrin in which hydrogen atoms in the porphyrin ring have been substituted with one or more cyano groups. Hydrogen atoms in the porphyrin ring may also be substituted with halogen atoms.

8 Claims, No Drawings

CYANO- AND POLYCYANOMETALLOPORPHYRINS AS CATALYSTS FOR ALKANE OXIDATION

BACKGROUND OF THE INVENTION

This invention relates to oxidation of alkanes using metalloporphyrins as catalysts, and more particularly to such processes in which cyano groups have been substituted for hydrogen in the porphyrin ligand.

The use of metalloporphyrins as catalysts for the oxidation of hydrocarbons with air in the liquid phase has been shown by the inventors in U.S. Pat. Nos. 4,895,680 and 4,895,682 with the further finding that halogenation of the porphyrin ring led to even more active and stable catalysts (U.S. Pat. Nos. 4,900,871, 4,970,348 and U.S. patent application Ser. No. 568,118). Since these discoveries we have been able to correlate increased electron withdrawal from halogenation of the porphyrin ring to increased catalytic air oxidation activity. J. E. Lyons and P. E. Ellis, Jr., *Catalysis Letters*, 8, 45 (1991).

Other functional groups besides halogens can lead to increased electron withdrawal from the metal center in metalloporphyrins. For example, cyano groups are known for their large electron withdrawing inductive effects and cyano containing metalloporphyrins with cyano groups in the beta or pyrrolic positions have been shown to be more easily reduced than their precursors without cyano substitution. R. J. Donohoe, M. Atamian and D. F. Bocian, *J. Amer. Chem. Soc.*, 109, 5593 (1987).

DESCRIPTION OF THE INVENTION

We have now found that cyanometalloporphyrins and cyano/halogenometalloporphyrins have utility as catalysts for the air oxidation of alkanes such as methane, ethane, propane, butanes, and the like.

The catalysts of the invention are particularly effective in the oxidation of alkanes, and alkenes, including cycloalkanes, substituted alkanes and alkenes and the like. The starting materials thus include straight and branched-chain compounds having from about 1 to 2 carbon atoms, preferably 1 to 10 carbon atoms, such as methane, ethane, propane, n-butane, isobutane, n-pentane, n-hexane, 2-methylpentane, 3-methylpentane, heptane, 2-methylheptane, 3-methylheptane, the corresponding alkene forms, and the like, as well as cycloalkanes and cycloalkenes having from about 5 to 20 carbon atoms, preferably 5 to 10 carbon atoms, such as cyclopentane, cyclohexane, cycloheptane, cyclooctane, the corresponding alkene forms, and the like. These compounds, if desired, may be substituted with various moieties, although care should be taken to exclude substituents which will adversely affect the activity of the catalyst.

The oxidation, which may be carried out in a generally known manner, is desirably conducted in the liquid phase, although this is not critical, using such organic solvents as benzene, acetic acid, acetonitrile, methyl acetate, or like solvents which are inert to the conditions of the reactions, or in a neat solution of the hydrocarbon if it is liquid, and under pressures ranging from about 15 to 1500 psig, preferably 30 to 750 psig, at temperature of from about 25° to 250° C., more preferably 70° to 180° C. Depending upon whether the hydrocarbon to be oxidized is a solid, liquid or gas, it is dissolved in or bubbled through the solvent, together with air or oxygen, in the presence of the catalyst used according to the invention, for periods of time sufficient to yield the desired oxidation product, generally from about 0.5 to 100 hours, and more preferably from 1 to 10 hours.

The choice of solvent, while not critical, can have an effect on the rates and selectivities obtained and should be carefully selected in order to optimize the desired results. For example, it has been found that solvents such as acetonitrile and acetic acid are often very effective for the oxidation of alkanes to form oxygen-containing compounds, whereas reactions carried out in solvents such as methyl acetate or benzene may occur more slowly. Thus, by routine experimentation, the optimum solvent for the particular process can be readily determined.

The ratios of the various reactants may vary widely, and are not critical. For example, the amount of catalyst employed can range from about $10^{-6}$ to $10^{-3}$ moles per mole of hydrocarbon such as alkane, and more preferably from about $10^{-5}$ to $10^{-4}$ mole of catalyst per mole of hydrocarbon, although other amounts are not precluded; while the amount of oxygen relative to the hydrocarbon starting material may also vary widely, generally $10^{-2}$ to $10^2$ moles of oxygen per mole of hydrocarbon. Care should be taken since some of the ratios fall within explosive limits. As a group, the catalysts are almost always soluble unless used in large excess. Thus, as a rule, the reactions are generally carried out homogeneously.

The process of the invention comprises contacting alkane with oxygen-containing gas in the presence of a metalloporphyrin in which 12.5 to 100 percent of the hydrogen atoms in the porphyrin ring have been replaced with cyano groups. Preferably, the metalloporphyrin contains as metal, iron, chromium, manganese, ruthenium, cobalt or copper.

In one embodiment, 4 to 28 percent of the hydrogen atoms in the porphyrin ring have been replaced with cyano groups and 0 to 72 percent of the hydrogen atoms in the porphyrin ring have been replaced with halogen. For example, in a porphyrin substituted with 20 fluorine atoms and 8 cyano groups, about 28 percent of the hydrogen atoms have been replaced with cyano groups and about 72 percent of the hydrogen atoms have been replaced with halogen atoms.

In one embodiment, 4 to 8 hydrogen atoms in the porphyrin ring have been substituted with cyano groups and 8 to 20 hydrogen atoms in the porphyrin ring have been substituted with halogen atoms.

In one embodiment, 1 to 8 of the pyrrolic hydrogens in the porphyrin ring have been replaced with cyano groups. In a further embodiment remaining halogens in the porphyrin ring have been replaced with halogen.

Preferably, all of the hydrogen atoms have been replaced either with cyano groups or halogen atoms, but this is not essential.

Specific catalysts useful according to the invention include cyanated meso-perfluorinatedalkylporphyrin, cyanated iron tetrakispentafluorophenylporphyrin and metallomesotetracyanoporphine.

Catalysts useful in the invention may be prepared by the following methods.

EXAMPLE 1

Zinc (tetrakispentafluorophenyl β-octabromoporphine) prepared by the bromination of Zn(tetrakis-pentafluorophenylporphine) with $Br_2$ in $CCl_4$ is treated with 9 equivalents of CuCN in quinoline at reflux for several hours. After chromatography several of the bromines are replaced with CN groups giving, according to the conditions $Zn(TPPF_{20}\beta\text{-}CN_{4\text{-}8})$. The zinc is removed by mild treatment with 1M HCl and recovered by chromatography on alumina. Metals can be inserted into this $H_2(TPPF_{20}\beta\text{-}CN_{4\text{-}8})$ by treatment with the metal salt in DMF, e.g., $FeCl_2$ in DMF, leading to $Fe(TPPF_{20}\beta\text{-}CN_{4\text{-}8})Cl$.

EXAMPLE 2

If the CuCN treatment is conducted under milder conditions some of the bromine groups can be retained leading to mixed bromo/cyano metalloporphyrins. Pyrrolic positions without cyano or bromo substitution can also be brominated, chlorinated or fluorinated leading to complexes of the general structure:

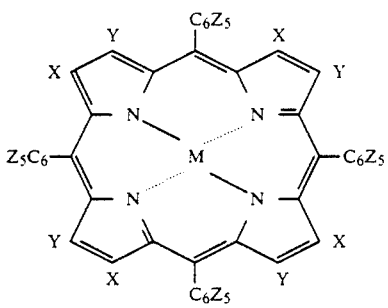

where

M is Fe, Cr, Mn, Ru, Co or Cu

X is CN

Y is CN, or Cl or Br or F

Z is H or Cl or F

EXAMPLE 3

The conversion to cyano derivatives as disclosed in the examples above can also be applied to meso-perfluorinatedalkylporphyrins as disclosed in U.S. patent application Ser. No. 568,118 filed Aug. 16, 1990, the disclosure of which is hereby incorporated by reference in this specification. The general structure of the products is:

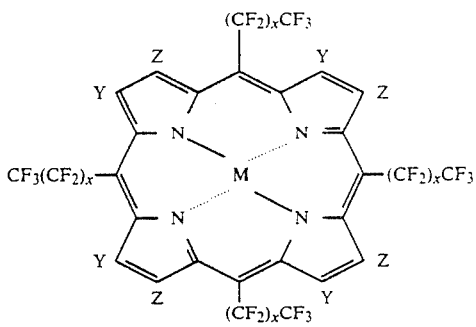

where,
M is Fe, Cr, Mn, Ru, Cu, Co
X is 0–6
Y is CN
Z is CN or Cl or Br or F

The invention will be further disclosed with reference to the following example.

EXAMPLE 4

The catalyst prepared as described in Example 1 is used as a catalyst for the oxidation of isobutane to t-butyl alcohol in the following manner. Isobutane (6–7 grams) is dissolved in 25 ml benzene containing the catalyst, and air is added to the desired pressure. Oxidation is carried out at the designated temperature for six hours. Gaseous and liquid products are analyzed by gas chromatography and mass spectrometry. Catalyst activity is expressed as "catalyst turnovers", i.e., moles of oxygen consumed/mole of catalyst. Selectivity is the moles of TBA per 100 moles of liquid product. Higher numbers of catalyst turnovers and/or greater selectivity are obtained with the catalyst of the invention as compared with otherwise similar catalyst which has not been substituted with cyano groups. Similar results are obtained when the catalysts of Examples 2 and 3 above are used as alkane oxidation catalysts.

The invention claimed is:

1. Process for oxidation of alkanes which comprises contacting alkane with oxygen-containing gas in the presence of metalloporphyrin in which hydrogen atoms in the porphyrin ring have been substituted with at least one cyano group.

2. Process according to claim 1 in which 1 to 8 of the pyrrolic hydrogens have been replaced with cyano groups.

3. Process according to claim 1 wherein the metalloporphyrin contains iron, chromium, manganese, ruthenium, cobalt or copper.

4. Process according to claim 2 in which remaining hydrogen atoms in the porphyrin ring have been replaced by halogens.

5. Process according to claim 4 in which 4 to 8 hydrogen atoms in the porphyrin ring have been replaced with cyano groups and in which 8 to 20 hydrogen atoms in the porphyrin ring have been replaced with halogen.

6. Process according to claim 1 in which the metalloporphyrin is a cyanated, meso-perfluorinated alkyl porphyrin.

7. Process according to claim 1 in which the metalloporphyrin is a cyanated iron tetrakis pentafluorophenylporphyrin.

8. Process according to claim 1 wherein the metalloporphyrin is a metallo mesotetracyanoporphine.

* * * * *

UNITED STATES PATENT AND TRADEMARK OFFICE
CERTIFICATE OF CORRECTION

PATENT NO. : 5,118,886
DATED : June 2, 1992
INVENTOR(S) : P. E. Ellis, Jr. and J. E. Lyons It is certified that error appears in the above-identified patent and that said Letters Patent is hereby corrected as shown below:

Column 1, after the title and before "Background of the Invention" insert the following as a separate paragraph:

"The Government of the United Stated States of America has rights in this invention pursuant to Cooperative Agreement No. DE-FC21-90MC26029 awarded by the U. S. Department of Energy."

Signed and Sealed this

Eighth Day of February, 1994

Attest:

BRUCE LEHMAN

*Attesting Officer*   *Commissioner of Patents and Trademarks*